(12) United States Patent
Ishii et al.

(10) Patent No.: US 6,306,634 B1
(45) Date of Patent: *Oct. 23, 2001

(54) ESTERASE GENE AND ITS USE

(75) Inventors: Takeshi Ishii; Satoshi Mitsuda, both of Takarazuka (JP)

(73) Assignee: Sumitomo Chemical Company, Limited, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/979,170

(22) Filed: Nov. 26, 1997

(30) Foreign Application Priority Data

Nov. 28, 1996 (JP) ................................. 8-318273
Dec. 24, 1996 (JP) ................................. 8-344075

(51) Int. Cl.[7] .................. C12N 9/18; C12N 15/00; C12N 1/20; C12Q 1/68

(52) U.S. Cl. ................ 435/197; 435/320.1; 435/6; 435/252.3; 536/23.1; 536/23.2

(58) Field of Search ............. 435/320.1, 69.1, 435/197, 6, 252.3; 536/23.1, 23.2

(56) References Cited

U.S. PATENT DOCUMENTS

| | | | |
|---|---|---|---|
| 4,607,013 | 8/1986 | Mitsuda et al. | 435/280 |
| 5,290,694 | 3/1994 | Nakanishi et al. | 435/198 |

FOREIGN PATENT DOCUMENTS

| | | |
|---|---|---|
| 0115860A2 | 8/1984 | (EP). |
| 0127386A2 | 12/1984 | (EP). |
| 0149674A1 | 7/1985 | (EP). |
| 0894868A2 | 2/1999 | (EP). |
| 2-190188 | 7/1990 | (JP). |
| 2190188 * | 7/1990 | (JP). |
| 5-056786 | 3/1993 | (JP). |

OTHER PUBLICATIONS

Gilbert, E., Enzyme Microb. Technol., vol. 15, pp. 634–645, 1993.*
Svendsen, A. et al., Biochem. Biophys. Acta, vol. 1259, pp. 9–17, 1995.*
Jorgensen et al., Journal of Bacteriology, vol. 173, No. 2, 559–567 (1991).
Sugihara et al., J. Biochem. 112, 598–603 (1992).
GenBank Database, Accession No. E04384 1997.
GenBank Database, Accession No. E02519 1997.

* cited by examiner

*Primary Examiner*—Ponnathapu Achutamurthy
*Assistant Examiner*—Peter P. Tung
(74) *Attorney, Agent, or Firm*—Birch, Stewart, Kolasch & Birch, LLP (57) ABSTRACT

An isolated esterase gene coding for an esterase capable of causing asymmetric hydrolysis of an organic carboxylic acid ester of a cyclopentenolone of formula I;

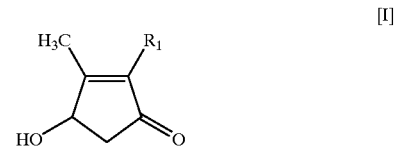

[I]

wherein $R_1$ is $C_1$–$C_{10}$ alkyl, $C_2$–$C_{10}$ alkenyl, $C_2$–$C_{10}$ alkynyl or $C_1$–$C_4$ haloalkyl, to produce the cyclopentenolone of formula I in (S)-form, and hybridizing to the base sequence of SEQ ID NO:1, is useful for the industrially favorable production of optically active cyclopentenolones of formula I which serve as the intermediates of drugs, agricultural chemicals or other active products.

7 Claims, 1 Drawing Sheet

Fig.1

ESTERASE GENE AND ITS USE

FIELD OF THE INVENTION

The present invention relates to an esterase gene and its use.

BACKGROUND OF THE INVENTION

Cyclopentenolones of formula I:

[I]

wherein $R_1$ is $C_1$–$C_{10}$ alkyl, $C_2$–$C_{10}$ alkenyl, $C_2$–$C_{10}$ alkynyl or $C_1$–$C_4$ haloalkyl, are useful as the important alcohol components in a group of ester compounds, commonly called "synthetic pyrethroids," having excellent insecticidal activity.

For example, the compound of formula II below, an ester of 4-hydroxy-3-methyl-2-(2-propynyl)cyclopent-2-en-1-one with 2,2,3,3-tetramethylcyclopropanecarboxylic acid, is an excellent insecticide having very strong knockdown activity and mortal activity (see, e.g., JP-B 50-15843/1975).

[II]

The cyclopentenolones of formula I include two kinds of optical isomers because they have an asymmetric carbon atom at position 4. In the case of synthetic pyrethroids containing such optical isomers as the alcohol components, it is well known that the difference in optical isomerism between these alcohol components makes a great difference in their insecticidal effects. For example, the compound of formula II above has been found to exhibit several times as excellent insecticidal activity in the case of an ester of (S)-4-hydroxy-3-methyl-2-(2-propynyl)cyclopent-2-en-1-one as in the case of an ester of the corresponding (R)-4-hydroxy-3-methyl-2-(2-propynyl)cyclopent-2-en-1-one.

For these reasons, there has been a great demand for the development of a method for separating and obtaining the optical isomers of cyclopentenolones of formula I as the intermediates of drugs, agricultural chemicals or other active products in an industrially favorable manner. In addition, for this purpose, in order to prepare a microorganism, for example, by a gene engineering technique, which microorganism can produce an excellent esterase capable of acting upon an organic carboxylic acid ester of a cyclopentenolone of formula I for asymmetric hydrolysis of the ester, the search of a gene coding for such an esterase has also been eagerly desired.

SUMMARY OF THE INVENTION

Under these circumstances, the present inventors have extensively studied and found an esterase gene coding for an esterase capable of acting upon an organic carboxylic acid ester of a cyclopentenolone of formula I for asymmetric hydrolysis of the ester to produce the cyclopentenolone in (S)-form with high optical purity, thereby completing the present invention.

Thus, the present invention provides:

1) An isolated esterase gene coding for an esterase capable of causing asymmetric hydrolysis of an organic carboxylic acid ester of a cyclopentenolone of formula I:

[I]

wherein $R_1$ is $C_1$–$C_{10}$ alkyl, $C_2$–$C_{10}$ alkenyl, $C_2$–$C_{10}$ alkynyl or $C_1$–$C_4$ haloalkyl, to produce the cyclopentenolone of formula I in (S)-form, and hybridizing to the base sequence of SEQ ID NO:1 (hereinafter refereed to as the present gene);

2) The isolated esterase gene according to item 1, wherein the homology of the gene to the base sequence of SEQ ID NO:1 is 90% or higher.

3) The isolated esterase gene according to item 1, having a base sequence coding for the amino acid sequence of SEQ ID NO:2.

4) The isolated esterase gene according to item 1, having the base sequence of SEQ ID NO:1.

5) A plasmid containing the isolated esterase gene of item 1, 2, 3 or 4 (hereinafter referred to as the present plasmid).

6) A transformant obtained by transformation with the plasmid of item 5 (hereinafter referred to as the present transformant).

7) The transformant according to item 6, which is a microorganism.

8) An esterase produced by a microorganism having the isolated esterase gene of item 1, 2, 3 or 4 (hereinafter referred to as the present esterase).

9) The esterase according to item 8, wherein the microorganism having the isolated esterase gene of item 1, 2, 3 or 4 is the transformant of item 6.

10) A process for producing en esterase, which comprises cultivating the transformant of item 6 to produce an esterase capable of causing asymmetric hydrolysis of an organic carboxylic acid ester of a cyclopentenolone of formula I:

[I]

wherein $R_1$ is $C_1$–$C_{10}$ alkyl, $C_2$–$C_{10}$ alkenyl, $C_2$–$C_{10}$ alkynyl or $C_1$–$C_4$ haloalkyl, to produce the cyclopentenolone of formula I in (S)-form (hereinafter referred to as the present production process).

11) A method for the optical resolution of a cyclopentenolone of formula I:

[I]

wherein $R_1$ is $C_1$–$C_{10}$ alkyl, $C_2$–$C_{10}$ alkenyl, $C_2$–$C_{10}$ alkynyl or $C_1$–$C_4$ haloalkyl, which comprises allowing the esterase of item 8 to act upon an organic carboxylic acid ester of the cyclopentenolone of formula I for asymmetric hydrolysis of the ester; and separating the cyclopentenolone of formula I in (S)-form from the ester of the corresponding enantiomer thereof.

12) The optical resolution method according to item 11, wherein the cyclopentenolone of formula I is 4-hydroxy-3-methyl-2-(2-propenyl)cyclopent-2-en-1-one.

13) The optical resolution method according to item 11, wherein the cyclopentenolone of formula I is 4-hydroxy-3-methyl-2-(2-propynyl)cyclopent-2-en-1-one.

DETAILED DESCRIPTION OF THE INVENTION

The present gene is an isolated esterase gene coding for an esterase capable of causing asymmetric hydrolysis of an organic carboxylic acid ester of a cyclopentenolone of formula I to produce the cyclopentenolone of formula I in (S)-form, and hybridizing to the base sequence of SEQ ID NO:1. The term "esterase" as used herein refers to an esterase as defined in a broad sense containing lipases.

The phrase "capable of causing asymmetric hydrolysis of an organic carboxylic acid ester of a cyclopentenolone of formula I to produce the cyclopentenolone of formula I in (S)-form" as used herein means that an esterase referred to by this phrase can cause asymmetric hydrolysis of an organic carboxylic acid ester of a cyclopentenolone of formula I such as 4-hydroxy-3-methyl-2-methylcyclopent-2-en-1-one, 4-hydroxy-3-methyl-2-ethyl-2-cyclopent-2-en-1-one, 4-hydroxy-3-methyl-2-(2-propenyl)-2-cyclopent-2-en-1-one, 4-hydroxy-3-methyl-2-(2,4-pentadienyl)-2-cyclopent-2-en-1-one, (±)-4-hydroxy-3-methyl-2-(1-methyl-2-propynyl)-2-cyclopent-2-en-1-one, 4-hydroxy-3-methyl-2-(2-propenyl)cyclopent-2-en-one, 4-hydroxy-3methyl-2-(1methyl-2-propynyl)cyclopent-2-en-1-one or 4-hydroxy-3-methyl-2-(2,2,2-trifluoroethyl)cyclopent-2-en-1-one, to produce the corresponding cyclopentenolone in (S)-form.

In the cyclopentenolone of formula I, variables have the following meanings.

The $C_1$–$C_{10}$ allyl represented by $R_1$ may include, for example, methyl, ethyl, pentyl and decyl.

The $C_2$–$C_{10}$ alkenyl represented by $R_1$ may include, for example, 2-propenyl, 1-methyl-2-propenyl, 2,4-pentadienyl, 2-heptenyl and 2-decenyl.

The $C_2$–$C_{10}$ alkynyl represented by $R_1$ may include, for example, 2-propynyl, 1-methyl-2-propynyl, 2-heptenyl and 2-decenyl.

The $C_1$–$C_4$ haloalkyl represented by $R_1$ may include, for example, 2,2,2-trifluoroethyl and 4,4,4-trifluorobutyl.

In the above organic carboxylic acid ester, the organic carboxylic acid may include, for example, $C_1$–$C_{10}$ saturated or unsaturated fatty acids, and pyrethroid acids.

The gene "hybridizing to the base sequence of SEQ ID NO:1" refers to a gene which can be visually detected by Southern hybridization as described, for example, in "Cloning and Sequence" (complied under the supervision of Itaru Watanabe, edited by Masahiro Sugiura, 1989, published by Noson Bunka-sha), using DNA having the base sequence of SEQ ID NO:1 as a probe. The gene may be DNA having the base sequence of SEQ ID NO:1 or DNA having a base sequence with the addition, deletion or replacement of one or more bases in the DNA having the base sequence of SEQ ID NO:1. For example, double-stranded DNA is dissociated into the complementary single-stranded DNAs by heat treatment at 95° C. for 1 minute or by alkali treatment with 0.5 M NaOH, 1.5 M NaCl, which are then left cooling on ice for 1 minute or subjected to neutralization with 0.5 M Tris-HCl (pH 7.0), 3.0 M NaCl so as to associate with single-stranded DNA or single-stranded RNA, which is complementary to the above single-stranded DNAs, to fall into a double-stranded state (i.e., hybridized state) again. Such DNA may be usually a gene having a base sequence with a high homology (e.g., about 90% or higher homology as a whole, although it may vary depending upon whether the region is closely related to an active site or a structure) to the base sequence of SEQ ID NO:1.

Homologies can be calculated with the homology search program developed by Pearson and Lipman (see, e.g., Pearson and Lipman, (1988), Proc. Natl. Acad. Sci. USA, 85, 2444). They can also be calculated with this kind of program contained in the Genetyx-Mac (available from Software Kaihatsu). For this purpose, a homology search program (fasta) found in the World Wide Web Service of the DNA Data Bank of Japan (DDBJ) can also be used.

A more specific example of the present gene is an esterase gene having a base sequence coding for the amino acid sequence of SEQ ID NO:2. Of course, the present gene may also include an esterase gene having the base sequence of SEQ ID NO:1.

The present gene can be obtained by the PCR method using genomic DNA prepared, for example, from a microorganism of the genus Burkholderia by an ordinary method (e.g., the method described in "Shin Saibo Kogaku Jikken Protocol" (edited by the Cancer Control Research Group, Medical Science Laboratory, Tokyo University, published by Shujun-sha, 1993) as a template and using a fragment of DNA having the base sequence of SEQ ID NO:1 (e.g., a combination of about 14 bp or more oligonucleotides complementary to the 5'-terminal sequence in the base sequence of SEQ ID NO:1 and about 14 bp or more oligonucleotides corresponding to the 3'-terminal sequence in the base sequence of SEQ ID NO:1; or a combination of about 14 bp or more oligonucleotides corresponding to the 5'-terminal sequence in the base sequence of SEQ ID NO:1 and about 14 bp or more oligonucleotides complementary to the 3'-terminal sequence in the base sequence of SEQ ID NO:1) as a primer.

The present gene can also be obtained by a method such as colony hybridization or plaque hybridization with a gene library constructed by the insertion of genomic DNA prepared, for example, from a microorganism of the genus Burkholderia by an ordinary method (e.g., the method described in "Shin Saibo Kogaku Jikken Protocol" (edited by the Cancer Control Research Group, Medical Science Laboratory, Tokyo University, published by Shujun-sha, 1993) into λ phages or plasmids, using a base sequence coding for the amino acid sequence of SEQ ID NO:2, preferably a 15 bp or more DNA fragment contained in the base sequence of SEQ ID NO:1, as a probe.

As the microorganism for use in the preparation of the present gene, among the microorganisms of the above genus, particularly preferred is *Burkholderia cepacia*, a specific example of which is *Burkholderia cepacia* strain SC-20.

*Burkholderia cepacia* strain SC-20 is a microorganism that has been found from the nature by the present inventors, and it has the bacteriological characteristics as shown in Table 1.

TABLE 1

| (1)  | Morphology                      | Rods          |
|------|---------------------------------|---------------|
| (2)  | Gram staining                   | Negative      |
| (3)  | Spore                           | –             |
| (4)  | Motility                        | +             |
| (5)  | Flagellar arrangement           | Single polar  |
| (6)  | Attitude to oxygen              | Aerobic       |
| (7)  | Oxidase test                    | +             |
| (8)  | Catalase test                   | +             |
| (9)  | OF test                         | O (oxidation) |
| (10) | Tone of colonies                | Yellow        |
| (11) | Fluorescent pigment formation   | –             |
| (12) | Water-soluble pigment formation | +             |
| (13) | PHB accumulation                | +             |
| (14) | Protocatechuate cleavage        | ortho         |
| (15) | Arginine dehydrolase            | –             |
| (16) | Growth at 40° C.                | +             |
| (17) | Denitrification                 | –             |
| (18) | Nitrate reduction               | –             |
| (19) | Gelatin liquefaction            | +             |
| (20) | Starch hydrolysis               | –             |
| (21) | Utilization of:                 |               |
|      | (a) Glucose                     | +             |
|      | (b) Xylose                      | +             |
|      | (c) Ribose                      | +             |
|      | (d) Rhamnose                    | +             |
|      | (e) Levulinate                  | +             |
|      | (f) Mesaconate                  | –             |
|      | (g) D-Tartrate                  | –             |
|      | (h) 2,3-Butylene glycol         | +             |
|      | (i) Tryptamine                  | –             |
| (22) | Quinone type                    | Q-8           |
| (23) | GC content of DNA in bacterial cells (mol %) | 68 |

These bacteriological characteristics are found to be consistent with those of *Burkholderia cepacia* when compared with the data in Bergey's Manual of Systematic Bacteriology, Vol. 1 (1984); Bergey's Manual of Determinative Bacteriology, Ninth edition (1994); Zhao et al., Int. J. Syst. Bacteriol., 45, p. 600 (1995); and Yabuuchi et al., Microbiol. Immunol., 36, p. 1251 (1992).

The present gene can be obtained by the PCR method using DNA prepared from the bacterial cells of *Escherichia coli* strain JM109/pAL108 as a template and using a fragment of DNA having the base sequence of SEQ ID NO:1 (e.g., a combination of about 14 bp or more oligonucleotides complementary to the 5'-terminal sequence in the base sequence of SEQ ID NO:1 and about 14 bp or more oligonucleotides corresponding to the 3'-terminal sequence in the base sequence of SEQ ID NO:1; or a combination of about 14 bp or more oligonucleotides corresponding to the 5'-terminal sequence in the base sequence of SEQ ID NO:1 and about 14 bp or more oligonucleotides complementary to the 3'-terminal sequence in the base sequence of SEQ ID NO:1) as a primer.

*E. coli* strain JM109/pAL108 is a transformant microorganism obtained by the incorporation of plasmid pAL108 containing the present gene (the present plasmid) into *E. coli* strain JM109 (the present transformant), and it has been deposited in the National Institute of Bioscience and Human-Technology, Agency of Industrial Science and Technology as "FERM-BP 5739"(accession date: Nov. 7, 1996).

The present plasmid can be easily constructed by incorporating the present gene obtained, for example, into a vector which has been usually used in host cells to be transformed, by an ordinary gene engineering technique. More specifically, for example, when *E. coli* as a microorganism is used as the host cell, the vector to be used may include pUC119 (available from Takara Shuzo) and pBluescriptII (available from Stratagene Cloning System).

The method for transforming a host cell with the present plasmid constructed may be a method usually used depending upon the host cell to be transformed, and for example, when *E. coli* as a microorganism is used as the host cell, it may include an ordinary method as described in "Molecular Cloning" (J. Sambrook et al., Cold Spring Harbor, 1989).

The selection of transformants is carried out as follows: For example, the host cell transformed with the present plasmid is first cultivated on an LB plate containing tributyrin, and those forming a clear zone are selected. The selected transformants are cultivated, and the resulting cultures are treated with an organic carboxylic acid ester of a cyclopentenolone of formula I. The reaction products are analyzed, so that transformants producing the cyclopentenolone of formula I in (S)-form with high optical purity may be selected.

More specifically, for example, 0.5 g of the acetic acid ester of (RS)-4-hydroxy-3-methyl-2-(2-propenyl)cyclopent-2-en-1-one and 8.0 ml of 50 mM phosphate buffer (pH 7.0) are put into a 100 ml sample bottle, and the mixture is preheated at 40° C. under stirring with a stirring bar for 10 minutes. To this mixture is added 1.0 ml of the above culture, and the reaction is effected at 40° C. under stirring with a stirring bar. After 30 minutes, the reaction mixture is taken in a volume of 50 μl, and the reaction is stopped by the addition of 1 ml of ethanol. For blanks, purified water is used instead of the culture, and the test is conducted in the same manner. The rate of decomposition is determined by gas chromatography. As the column for analysis, 10% silicone DC-QF-1, 2.6 m long, is used, and the analysis is carried out with GC-14A (available from Shimazu Seisakusho) under the following conditions: column temperature, 150° C.; injection temperature, 170° C.; detection temperature, 170° C.; and detector, FID. For the enzyme titer, the amount of enzyme releasing 1 μmol of (S)-4-hydroxy-3-methyl-2-(2-propenyl)cyclopent-2-en-1-one for 1 minute is defined as 1 unit. The reaction mixture is further extracted with methyl isobutyl ketone, and the extract is examined for the optical purity of (S)-4-hydroxy-3-methyl-2-(2-propenyl)cyclopent-2-en-1-one by the HPLC analysis. In the analysis, columns for optical isomer analysis OA4100 (4.0 mm I.D.×25 cm) available from Sumika Bunseki Center are used. As the eluent, a mixture of hexane, 1,2-dichloroethane and ethanol at a ratio of 100:20:1 can be used. The optical isomer ratio may be determined at a flow rate of 1.0 ml/min. with an absorbance at 230 nm as an index.

More particularly, from the selected transformants, plasmids contained in the transformants are prepared, and the restriction endonuclease maps of the plasmids thus prepared are constructed by an ordinary method as described, for example, in "Molecular Cloning" (J. Sambrook et al., Cold Spring Harbor, 1989). It can also be determined whether the desired present gene is contained or not by a method such as base sequence analysis, Southern hybridization or Western hybridization.

In this manner, the present transformants can be obtained and cultivated to produce the present esterase (the present production process).

When the transformants are microorganisms, the transformants are cultivated with various kinds of media suitably containing carbon sources, nitrogen sources, organic salts and/or inorganic salts, and other additives, which have been used for preparing the ordinary cultures of microorganisms. The carbon sources may include glucose, glycerol, dextrin, sucrose, organic acids, animal and vegetable oils, and molasses. The nitrogen sources may include organic and inorganic nitrogen sources such as broth, peptone, yeast extract, malt extract, soy bean powder, corn steep liquor, cotton seed powder, dry yeast, casamino acid, sodium nitrate and urea. The organic and inorganic salts may include chlorides, sulfates, acetates, carbonates and phosphates of elements such as potassium, sodium, magnesium, iron, manganese, cobalt and zinc, specific examples of which are sodium chloride, potassium chloride, magnesium sulfate, ferrous sulfate, manganese sulfate, cobalt chloride, zinc sulfate, copper sulfate, sodium acetate, calcium carbonate, sodium carbonate, potassium monohydrogenphosphate and potassium dihydrogenphosphate.

Cultures are prepared by an ordinary method for microorganisms, and they can be in the form of either solid cultures or liquid cultures (e.g., shaking cultures using test tubes or reciprocating shakers, and other cultures using jar fermenters or fermentation tanks). In particular, when jar fermenters are used, it is necessary to introduce aseptic air thereinto, usually at a rate of about 0.1 to about 2 times the culture volume per minute. The incubation temperature may be suitably altered within a range to ensure the growth of microorganisms. For example, cultures are preferably incubated at a temperature of about 15° C. to about 40° C. under the control of medium pH within the range of about 6.0 to about 8.0. The incubation period may vary on various conditions of incubation, and the preferred incubation period is usually in the range of about 1 to about 5 days.

The present esterase has the following characteristics:
1) The molecular weight (determined by SDS-PAGE) is about 40 kilo-daltons;
2) The reaction can be effected in the range of at least about 15° C. to about 60° C., preferably about 25° C. to about 40° C.;
3) The reaction can be effected in the pH range of about 4 to about 9, preferably about 6 to about 8;
4) It is capable of causing asymmetric hydrolysis of an organic carboxylic acid ester of a cyclopentenolone of formula I to produce the cyclopentenolone of formula I in (S)-form;
5) It can also be obtained by cultivating non-transformants, for example, of a microorganism of the genus Burkholderia (particularly preferred is *Burkholderia cepacia*, a specific example of which is *Burkholderia cepacia* stain SC-20). Of course, as described above, it can also be obtained by cultivating the transformants which have been prepared by transformation with a plasmid containing the present gene.

The present esterase may be utilized for the enzyme reaction in the form of a culture containing the same, but may also be utilized for the enzyme in the form of a crude enzyme separated from the culture or in the form of a purified enzyme. The crude enzyme may be separated by an ordinary method, for example, in which bacterial cells are disrupted by ultrasonic disintegration, trituration with glass beads or alumina, homogenization or disruption with a French press, enzyme treatment with lysozyme, and the desired fraction is obtained from the disrupted bacterial cells by salt deposition with ammonium sulfate or any other salt; precipitation with an organic solvent or an organic polymer such as polyethylene glycol; chromatography such as ion exchange chromatography, hydrophobic chromatography, gel filtration chromatography, affinity chromatography or any other chromatography; or electrophoresis. If necessary, these techniques can be used in combination.

Furthermore, the present esterase can also be utilized for the enzyme reaction in the form of an immobilized product which has been obtained by insolubilizing the esterase by a method of immobilization, such as a carrier binding technique in which the esterase is attached to a carrier by covalent bonding, ion bonding or absorption; or an entrapment technique in which the esterase is entrapped into the network structure of a polymer; and then by processing the insolubilized esterase into an easily separable state.

The present esterase can be utilized, for example, in the optical resolution of a cyclopentenolone of formula I. That is, the present esterase can be allowed to act upon an organic carboxylic acid ester of a cyclopentenolone of formula I for asymmetric hydrolysis of the ester, so that the cyclopentenolone of formula I in (S)-form is separated from the ester of the corresponding enantiomer thereof. In such a resolution, esters in racemic form are usually used as the starting material.

Specific examples of the cyclopentenolone of formula I are 4-hydroxy-3-methyl-2-(2-propenyl)cyclopent-2-en-1-one and 4-hydroxy-3-methyl-2-(2-propynyl)cyclopent-2-en-1-one.

The reaction temperature is, for example, in the range of about 15° C. to about 60° C., preferably about 25° C. to about 40.C. The reaction pH is, for example, in the range of about 4 to about 9, preferably about 6 to about 8. The reaction time is, for example, in the range of about 5 minutes to about 96 hours.

The cyclopentenolone of formula I in (S)-form and the ester of the corresponding enantiomer thereof can be recovered from the reaction mixture by any method generally known in the art. For example, procedures such as extraction with a solvent, fractional distillation and column chromatography can be suitably employed. Specifically, the reaction mixture is extracted with an organic solvent such as ether, ethyl acetate or benzene, and the extract is subjected to fractional distillation, or to silica gel chromatography, followed by extraction, so that the cyclopentenolone of formula I in (S)-form is separated from the ester of the corresponding enantiomer thereof.

EXAMPLES

The present invention will be further illustrated by the following examples; however, the present invention is not limited to these examples in any way whatsoever.

Example 1

(Preparation of Genomic DNA)

A culture of *Burkholderia cepacia* strain SC-20 was grown on a medium (Bacto tryptone (available from Difco Laboratories Incorporated), 10 g; Bacto yeast extract (available from Difco Laboratories Incorporated), 5 g; NaCl, 5 g/l; hereinafter referred to simply as LB medium) at 30° C. for 12 hours, and then harvested by centrifugation at 6000 rpm for 10 minutes to collect the bacterial cells.

The collected bacterial cells were suspended in a solution (10 mM Tris-HCl (pH 8.0), 1 mM EDTA-NaOH (pH 8.0), 10 mM NaCl; hereinaftr referred to simply as TEN solution) containing 1 mgtml lysozyme chloride (available from Seikagaku Kogyo) and 25 μg/ml RNaseA (available from Sigma Aldrich Japan), and then incubated at 37° C. for 20 minutes. Thereafter, sodium dodecylsulfate was added to a final concentration of 1% (w/v), and incubation was continued at 55° C. for 10 minutes. Then, phenol saturated with TE [10 mM Tris-HCl (pH 8.0), 1 mM EDTA (pH 8.0)] was added in the same volume. The mixture was slowly stirred and then centrifuged at 10,000 rpm for 10 minutes to collect the upper layer, to which a TE-saturated phenol-chloroform solution was added in the same volume. The mixture was slowly stirred and then centrifuged at 10,000 rpm for 10 minutes to collect the upper layer, to which a 3M ammonium acetate solution was added in a 1/10-fold volume and then ethanol, in a 2-fold volume. The DNA being deposited was taken by rolling it up round a glass rod. This DNA was rinsed with 70% (v/v) ethanol, and then rinsed again with 80% (v/v) ethanol and 100% ethanol, successively, followed by air drying. The DNA thus obtained was suspended in a TEN solution containing 25 μg/ml RNascA (available from Sigma Aldrich Japan) and 20 μg/ml Proteinase K (available from Boehringer Mannheim), and then incubated at 37° C. for 12 hours, to which a TE-saturated phenol-chloroform solution was added in the same volume. The mixture was slowly stirred and then centrifuged at 10,000 rpm for 10 minutes to collect the upper layer, to which a 3M ammonium acetate solution was added in a 1/10-fold volume and then ethanol, in a 2-fold volume. The DNA being deposited was taken by rolling it up round a glass rod. This DNA was rinsed with 70% (v/v) ethanol, and then rinsed again with 80% (v/v) ethanol and 100% ethanol, successively, followed by air drying. The DNA thus obtained was dissolved in 10 ml of TE solution containing 25 μg/ml RNaseA, and the solution was dialyzed twice against 2 L of TE solution. Thus, about 1.6 mg of genomic DNA was obtained from 100 ml of the culture.

Example 2
(Preparation of Genomic DNA Library)
Fifty micrograms of the genomic DNA obtained above was digested with the restriction endonuclease Eco RI at 37° C. for 1 hour. Separately, expression vector pUC19 (available from Tea Shuzo) was digested with the restriction nuclease Eco RI at 37° C. for 1 hour, followed by alkaline phosphatase treatment. These digests were ligated together with a ligation kit (available from Takara Shuzo) at 16° C. overnight. After completion of the ligation, the ligation solution was used for the transformation of E. coli strain JM109 competent cells (available from Toyo Boseki). The transformed E. coli cells were grown on a medium (Bacto tryptone (available form Difco Laboratories Incorporated), 20 g; Bacto yeast extract (available from Difco Laboratories Incorporated), 10 g; 1 M NaCl, 10 ml; 1 M KCl, 2.5 ml; 1 M $MgSO_4$, 10 ml; 1 M $MgCl_2$, 10 ml; 2 M Glucose, 10 ml per liter (pH=7.4); hereinafter referred to simply as SOC medium) at 37° C. for 2 hours and then grown on an LB medium containing 20 ml of 50 mg/l ampicillin at 37° C. overnight. The resulting culture was plated on an LB medium containing 1 mM isopropyl thio-β-D-galactoside (hereinafter referred to simply as ITPG), 1.0% tributyrin and 50 mg/l ampicillin, followed by growing at 37° C. After the growth for a few days, 29 strains forming a clear zone were selected. From the selected transformants, a plasmid as prepared and examined for the inserted fragment with restriction endonucleases, resulting in a transformant having inserted 3.5 kb Eco RI fragment. The plasmid thus obtained was designated pAL101.

Figure 1:
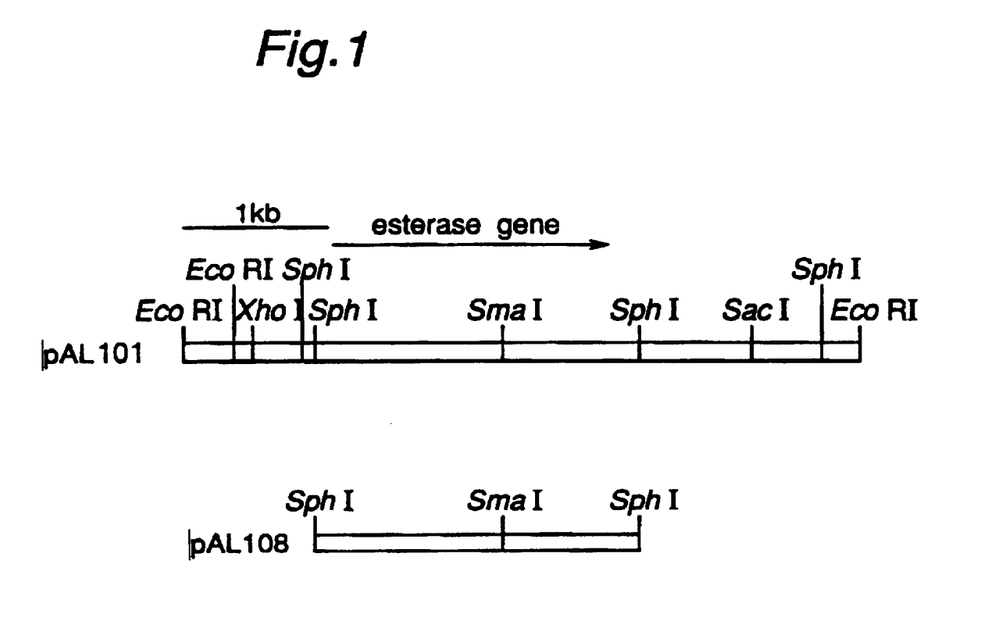
FIG. 1 is a diagram showing the restriction endonuclease maps of pAL101 and pAL108, which are specific examples of the present plasmids.

Example 3
(Restriction Endonuclease Analysis and Base Sequence Analysis)
The plasmid pAL101 obtained in Example 2 was analyzed with restriction endonucleases to produce a restriction endonuclease map as shown in FIG. 1. For the present gene contained in pAL101, the base sequence was determined with PRISM kit and automatic base sequence analyzer 373A (both available from Perkin Elmer Japan). The resulting base sequence was analyzed with Genetyx-Mac/ATSQ and Genetyx-Mac (both available from Software Kaihatsu). The base sequence of the esterase gene obtained by the analysis is shown by SEQ ID NO:1 in the Sequence Listing.

Example 4
(Subcloning)
Various plasmids were constructed by contracting the 3.5 kb Eco RI fragment present in the plasmid pAL101 obtained in Example 2. These plasmids were introduced and transformed into E. coli strain JM109 competent cells (available from Toyo Boseki) according to a method as described in Example 2. The transformed E. coli cells were cultivated on an LB medium containing tributyrin. The plasmid pAL108 having deleted genetic regions irrelevant to the production of the present esterase was constructed by detecting the formation of a clear zone. The plasmid pAL108 had inserted 1.7 kb Sph I fragment.

Example 5
(Optical Selectivity I of Esterase)
A culture of the transformant obtained in Examples 3 and 4 was grown on 100 ml of LB medium containing 50 mg/l of ampicillin and 50 mg/l of 1 mM isopropyl thio-β-D-galactoside (hereinafter referred to simply IPTG) at 37° C. for 16 hours, and then harvested by centrifugation at 6000 rpm for 10 minutes to collect the bacterial cell.
The bacterial cells obtained were suspended in 20 ml of 200 mM phosphate buffer. The suspension was allowed to act upon 1 g of the acetic acid ester of (RS)-4-hydroxy-3-methyl-2-(2-propenyl)cyclopent-2-en-1-one, and the resulting (S)-4-hydroxy-3-methyl-2-(2-propenyl)cyclopent-2-en-1-one was analyzed. The analysis of (S)-4-hydroxy-3-methyl-2-(2-propenyl)cyclopent-2-en-1-one was carried our as follows:
First, 0.5 g of the methyl ester of (RS)-4-hydroxy-3-methyl-2-(2-propenyl)cyclopent-2-en-1-one and 8.0 ml of 50 mM phosphate buffer (pH 7.0) were put in a 100 ml sample bottle, and preheated under stirring with a stirring bar at 40° C. for 10 minutes. To this mixture was added 1.0 ml of the above culture, and the reaction was effected at 40° C. under stirring with a stirring bar. After 30 minutes, the reaction mixture was taken in a volume of 50 μl, and the reaction was stopped by the addition of 1 ml of ethanol. For blanks, purified water was used instead of the culture, and the test was conducted in the same manner. The rate of decomposition was determined by gas chromatography. As the column for analysis, 10% silicone DC-QF-1, 2.6 m long, was used, and the analysis was carried out with GC-14A (from Shimazu Seisakusho) under the following conditions: column temperature, 150° C.; injection temperature, 170° C.; detection temperature, 170° C.; and detector, FID. For the enzyme titer, the amount of enzyme releasing 1 μmol of (RS)-4-hydroxy-3-methyl-2-(2-propenyl)cyclopent-2-en-1-one for 1 minute is defined as 1 unit. The reaction mixture was further extracted with methyl isobutyl ketone, and the extract was examined for optical purity by the HPLC analysis. In the analysis, a column for optical isomer analysis OA-4100 (4.0 mm I.D.×25 cm) available from Sumika Bunseki Center was used. As the eluent, a mixture of hexane, 1,2-dichloroethane and ethanol at a ratio of 100:20:1 was used. The optical isomer ratio was determined at a flow rate of 1.0 ml/min with an absorbance at 230 mm as an index.

Based on the results of the above analysis, the rate of hydrolysis and optical selectivity were calculated and are shown in Table 2.

TABLE 2

| Transformant | Rate of hydrolysis (%) | Optical isomer ratio [(S)/(R)] of released 4-hydroxy-3-methyl-2-(2-propenyl)cyclopent-2-en-1-one |
|---|---|---|
| JM109/pAL108 | 43 | 95/5 |

As can be seen from Table 3, *E. coli* strain JM109/pAL108, which is a transformant containing the inserted 1.7 kbp Sph I fragment, produces an esterase capable of causing asymmetric hydrolysis of the acetic acid ester of (RS)-4hydroxy-3-methyl-2-(2-propenyl)cyclopent-2-en-1-one to produce (S)-4-hydroxy-3-methyl-2-(2-propenyl)cyclopent-2-en-1-one.

Example 6

(Optical Selectivity II of Esterase)

The acetic acid ester of (RS)-4-hydroxy-3-methyl-2-(2-propynyl)cyclopent-2-en-1-one was used as the substrate, and the same experiments as described in Example 4 were made. The results are shown in Table 3.

TABLE 3

| Transformant | Rate of hydrolysis (%) | Optical isomer ratio [(S)/(R)] of released 4-hydroxy-3-methyl-2-(2-propenyl)cyclopent-2-en-1-one |
|---|---|---|
| JM109/pAL108 | 22 | 94/6 |

As described above, the present invention made it possible to provide a gene coding for an esterase capable of acting upon an organic carboxylic acid ester of a cyclopentenolone of formula I for asymmetric hydrolysis of the ester to produce the cyclopentenolone of formula I in (S)-form with high optical purity.

What is claimed is:

1. An isolated polynucleotide coding for an esterase capable of causing asymmetric hydrolysis of an organic carboxylic acid ester of a cyclopentenolone of formula I:

[I]

wherein $R_1$ is $C_1$–$C_{10}$ alkyl, $C_2$–$C_{10}$ alkenyl, $C_2$–$C_{10}$ alkynyl or $C_1$–$C_4$ haloalkyl, to produce the cyclopentenolone of formula I in (S)-form, and having:
(a) a base sequence of SEQ ID NO:1,
(b) a base sequence coding for the amino acid sequence of SEQ ID NO:2, or
(c) a base sequence of SEQ ID NO:1 with the addition, deletion or substitution of one or more bases, wherein when a double-stranded DNA of said base sequence is dissociated into complementary single-stranded DNAs by heat treatment at 95° C. for 1 minute or alkali treatment with 0.5 M NaOH, 1.5 M NaCl, said single-stranded DNAs hybridize with the base sequence of SEQ ID NO:1 when cooled ice for 1 minute or subjected to neutralization with 0.5 M Tris-HCl, pH 7.0, 3.0 M NaCl, and wherein the homology as a whole, of the polynucleotide is 90% to SEQ ID NO: 1 or higher.

2. An isolated polynucleotide coding for an esterase capable of causing asymmetric hydrolysis of an organic carboxylic acid ester of a cyclopentenolone of formula I:

[I]

wherein $R_1$ is $C_1$–$C_{10}$ alkyl, $C_2$–$C_{10}$ alkenyl, $C_2$–$C_{10}$ alkynyl or $C_1$–$C_4$ haloalkyl, to produce the cyclopentenolone of formula I in (S)-form, and having a base sequence coding for the amino acid sequence of SEQ ID NO:2.

3. An isolated polynucleotide coding for an esterase capable of causing asymmetric hydrolysis of an organic carboxylic acid ester of a cyclopentenolone of formula I:

[I]

wherein $R_1$ is $C_1$–$C_{10}$ alkyl, $C_2$–$C_{10}$ alkenyl, $C_2$–$C_{10}$ alkynyl or $C_1$–$C_4$ haloalkyl, to produce the cyclopentenolone of formula I in (S)-form, and having the base sequence of SEQ ID NO:1.

4. A plasmid containing the polynucleotide of claims 1, 2, or 3.

5. A transformed host cell obtained by transformation with the plasmid of claim 4.

6. The transformed host cell according to claim 5, which is a microorganism.

7. A process for producing an esterase, which comprises cultivating the transformed host cell of claim 5 to produce an esterase capable of causing asymmetric hydrolysis of an organic carboxylic acid ester of a cyclopentenolone of formula I:

[I]

wherein $R_1$ is $C_1$–$C_{10}$ alkyl, $C_2$–$C_{10}$ alkenyl, $C_2$–$C_{10}$ alkynyl or $C_1$–$C_4$ haloalkyl, to produce the cyclopentenolone of formula I in (S)-form; and isolating the esterase.

* * * * *

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
      (A) LENGTH: 1179 base pairs
      (B) TYPE: nucleic acid
      (C) STRANDEDNESS: double
      (D) TOPOLOGY: linear    (ii) MOLECULE TYPE: DNA (genomic)

(vi) ORIGINAL SOURCE:
      (A) ORGANISM: Burckholderia cepacia
      (B) STRAIN: SC-20

(ix) FEATURE:
      (A) NAME/KEY: CDS
      (B) LOCATION: 1..1179

(xi) SEQUENCE DESCRIPTION: SEQ ID NO: 1:

```
ATG ATC CCC AAC CGC GCA TCA TCC CGG CAG CCG TCG ACC GAT CCC GCA        48
Met Ile Pro Asn Arg Ala Ser Ser Arg Gln Pro Ser Thr Asp Pro Ala
 1               5                  10                  15

CTC GCC GAG CGC GTC GAT GCG GTA CTG TCC CGT CAA CTC GAA ACA CAT        96
Leu Ala Glu Arg Val Asp Ala Val Leu Ser Arg Gln Leu Glu Thr His
                20                  25                  30

CGC CTC GTT GGT GTG GTC GTC CTG ATC GCA CGC GAC GGC GAA CTC GTC       144
Arg Leu Val Gly Val Val Val Leu Ile Ala Arg Asp Gly Glu Leu Val
            35                  40                  45

TAT CGC CGC GCG GCC GGG TTC GCC GAT CGC GAA GCG CGC ACG CCG ATG       192
Tyr Arg Arg Ala Ala Gly Phe Ala Asp Arg Glu Ala Arg Thr Pro Met
        50                  55                  60

CGC GAG GAC ACG CTG TTC AGG CTC GCA TCG GTG ACG AAG CCG ATC GTC       240
Arg Glu Asp Thr Leu Phe Arg Leu Ala Ser Val Thr Lys Pro Ile Val
```

-continued

| | | | | | | | | | | | | | | | |
|---|---|---|---|---|---|---|---|---|---|---|---|---|---|---|---|
| | 65 | | | | 70 | | | | 75 | | | | 80 | | |
| TCG | GCG | GCC | GCG | ATG | GCG | CTC | GTC | GCG | CAA | CAC | AAG | CTG | TCG | CTC | GAC | 288 |
| Ser | Ala | Ala | Ala | Met | Ala | Leu | Val | Ala | Gln | His | Lys | Leu | Ser | Leu | Asp | |
| | | | | 85 | | | | 90 | | | | 95 | | | |
| GAC | GAC | GTC | ACG | CGC | TGG | CTG | CCC | GAG | TTC | CGC | CCG | GCG | CTG | CGC | GAC | 336 |
| Asp | Asp | Val | Thr | Arg | Trp | Leu | Pro | Glu | Phe | Arg | Pro | Ala | Leu | Arg | Asp | |
| | | | 100 | | | | 105 | | | | 110 | | | | |
| GGC | AGC | GTG | CCG | GTG | ATC | AGG | GTG | CGC | CAC | CTG | CTC | ACG | CAC | ACG | GCC | 384 |
| Gly | Ser | Val | Pro | Val | Ile | Arg | Val | Arg | His | Leu | Leu | Thr | His | Thr | Ala | |
| | | 115 | | | | 120 | | | | 125 | | | | | |
| GGC | CTC | GGC | TAT | CGC | TTC | ACG | GAA | GCC | GAC | GCG | ACC | GGC | CCC | TAT | GCG | 432 |
| Gly | Leu | Gly | Tyr | Arg | Phe | Thr | Glu | Ala | Asp | Ala | Thr | Gly | Pro | Tyr | Ala | |
| | 130 | | | | 135 | | | | 140 | | | | | | |
| CGC | GCG | GGC | GCC | TCC | GAC | GGG | CTC | GAT | GCC | GCA | TCG | ATC | ACG | CTC | GCC | 480 |
| Arg | Ala | Gly | Ala | Ser | Asp | Gly | Leu | Asp | Ala | Ala | Ser | Ile | Thr | Leu | Ala | |
| 145 | | | | 150 | | | | 155 | | | | 160 | | | |
| GAA | AAC | CTG | CGC | AGG | ATC | GCG | AGC | GTG | CCG | CTG | CAG | TTC | GCG | CCG | GGA | 528 |
| Glu | Asn | Leu | Arg | Arg | Ile | Ala | Ser | Val | Pro | Leu | Gln | Phe | Ala | Pro | Gly | |
| | | | 165 | | | | 170 | | | | 175 | | | | |
| ACC | GGC | TGG | AAC | TAT | TCG | CTT | TCC | ATC | GAC | GTG | GTC | GGC | GCG | CTG | ATC | 576 |
| Thr | Gly | Trp | Asn | Tyr | Ser | Leu | Ser | Ile | Asp | Val | Val | Gly | Ala | Leu | Ile | |
| | | 180 | | | | 185 | | | | 190 | | | | | |
| GAG | GCC | GTC | AGC | GGG | CTG | CCG | CTC | GCC | GAC | GCC | ATC | GAC | ACG | CTC | GTG | 624 |
| Glu | Ala | Val | Ser | Gly | Leu | Pro | Leu | Ala | Asp | Ala | Ile | Asp | Thr | Leu | Val | |
| | 195 | | | | 200 | | | | 205 | | | | | | |
| CTC | CGC | CCG | CTC | GGC | GCC | CGC | GAC | ACG | GGA | TTC | GTC | GCA | CGC | GAC | GCC | 672 |
| Leu | Arg | Pro | Leu | Gly | Ala | Arg | Asp | Thr | Gly | Phe | Val | Ala | Arg | Asp | Ala | |
| 210 | | | | 215 | | | | 220 | | | | | | | |
| GCG | CGG | CTC | GCG | ACG | CCC | TAC | GTC | AAC | GAC | ACA | CCG | CAA | CCG | CAC | CGG | 720 |
| Ala | Arg | Leu | Ala | Thr | Pro | Tyr | Val | Asn | Asp | Thr | Pro | Gln | Pro | His | Arg | |
| 225 | | | | 230 | | | | 235 | | | | 240 | | | |
| CTC | GCC | GAA | AAC | GAG | ACC | GTA | CCC | ATC | TTC | GAC | GGA | ACC | GTC | GGC | GTG | 768 |
| Leu | Ala | Glu | Asn | Glu | Thr | Val | Pro | Ile | Phe | Asp | Gly | Thr | Val | Gly | Val | |
| | | | 245 | | | | 250 | | | | 255 | | | | |
| ACG | TAT | TCG | CCG | TCG | CGC | GCG | CTC | GAC | GCG | GAT | GCG | TTC | CCG | TCG | GGC | 816 |
| Thr | Tyr | Ser | Pro | Ser | Arg | Ala | Leu | Asp | Ala | Asp | Ala | Phe | Pro | Ser | Gly | |
| | | 260 | | | | 265 | | | | 270 | | | | | |
| GGC | GCC | GGG | ATG | GTC | GGC | ACC | GCC | GGC | GAC | GTG | CTG | AAC | CTG | CTG | GAC | 864 |
| Gly | Ala | Gly | Met | Val | Gly | Thr | Ala | Gly | Asp | Val | Leu | Asn | Leu | Leu | Asp | |
| | 275 | | | | 280 | | | | 285 | | | | | | |
| ACG | CTG | CGC | GCG | GGC | GGC | GGT | TCG | CTG | CTG | CCG | GCC | GAC | CTG | GTC | GAC | 912 |
| Thr | Leu | Arg | Ala | Gly | Gly | Gly | Ser | Leu | Leu | Pro | Ala | Asp | Leu | Val | Asp | |
| | 290 | | | | 295 | | | | 300 | | | | | | |
| GAG | ATG | GGC | CGC | GCC | CAC | ACC | GGC | AAC | CTC | GAA | TTG | CCC | GAC | CTG | CCC | 960 |
| Glu | Met | Gly | Arg | Ala | His | Thr | Gly | Asn | Leu | Glu | Leu | Pro | Asp | Leu | Pro | |
| 305 | | | | 310 | | | | 315 | | | | 320 | | | |
| GGC | GCG | GGG | TTC | GGA | ATC | GGG | TTC | TCG | GTA | TTG | CGC | GAC | CCG | CTC | GCG | 1008 |
| Gly | Ala | Gly | Phe | Gly | Ile | Gly | Phe | Ser | Val | Leu | Arg | Asp | Pro | Leu | Ala | |
| | | | 325 | | | | 330 | | | | 335 | | | | |
| GCG | GCA | TCG | CCG | GAG | TCG | GTG | GGC | ACG | TGG | CGC | TGG | GGC | GGC | GTG | TAC | 1056 |
| Ala | Ala | Ser | Pro | Glu | Ser | Val | Gly | Thr | Trp | Arg | Trp | Gly | Gly | Val | Tyr | |
| | | | 340 | | | | 345 | | | | 350 | | | | |
| GGG | CAT | TCG | TGG | TTC | GTC | GAC | CGC | GCC | CGG | GGG | CTC | ACC | GTC | GTG | TCG | 1104 |
| Gly | His | Ser | Trp | Phe | Val | Asp | Arg | Ala | Arg | Gly | Leu | Thr | Val | Val | Ser | |
| | | 355 | | | | 360 | | | | 365 | | | | | |
| CTG | TCG | AAC | ACG | CTT | TAC | GAA | GGG | ATG | AAC | GGC | CAG | TAC | ACG | ATC | GAT | 1152 |
| Leu | Ser | Asn | Thr | Leu | Tyr | Glu | Gly | Met | Asn | Gly | Gln | Tyr | Thr | Ile | Asp | |
| | 370 | | | | 375 | | | | 380 | | | | | | |
| CTG | CGC | GAC | GCG | ATC | TAC | GGC | GCC | GGC | | | | | | | | 1179 |
| Leu | Arg | Asp | Ala | Ile | Tyr | Gly | Ala | Gly | | | | | | | | |

```
Leu Arg Asp Ala Ile Tyr Gly Ala Gly
385                 390
```

(2) INFORMATION FOR SEQ ID NO: 2:

(i) SEQUENCE CHARACTERISTICS:
        (A) LENGTH: 393 amino acids
        (B) TYPE: amino acid
        (D) TOPOLOGY: linear     (ii) MOLECULE TYPE: protein     (xi) SEQUENCE DESCRIPTION: SEQ ID NO: 2:

```
Met Ile Pro Asn Arg Ala Ser Ser Arg Gln Pro Ser Thr Asp Pro Ala
 1               5                  10                  15

Leu Ala Glu Arg Val Asp Ala Val Leu Ser Arg Gln Leu Glu Thr His
             20                  25                  30

Arg Leu Val Gly Val Val Leu Ile Ala Arg Asp Gly Glu Leu Val
         35                  40                  45

Tyr Arg Arg Ala Ala Gly Phe Ala Asp Arg Glu Ala Arg Thr Pro Met
 50                  55                  60

Arg Glu Asp Thr Leu Phe Arg Leu Ala Ser Val Thr Lys Pro Ile Val
65                  70                  75                  80

Ser Ala Ala Ala Met Ala Leu Val Ala Gln His Lys Leu Ser Leu Asp
                 85                  90                  95

Asp Val Thr Arg Trp Leu Pro Glu Phe Arg Pro Ala Leu Arg Asp
             100                 105                 110

Gly Ser Val Pro Val Ile Arg Val Arg His Leu Leu Thr His Thr Ala
             115                 120                 125

Gly Leu Gly Tyr Arg Phe Thr Glu Ala Asp Ala Thr Gly Pro Tyr Ala
    130                 135                 140

Arg Ala Gly Ala Ser Asp Gly Leu Asp Ala Ala Ser Ile Thr Leu Ala
145                 150                 155                 160

Glu Asn Leu Arg Arg Ile Ala Ser Val Pro Leu Gln Phe Ala Pro Gly
                165                 170                 175

Thr Gly Trp Asn Tyr Ser Leu Ser Ile Asp Val Val Gly Ala Leu Ile
            180                 185                 190

Glu Ala Val Ser Gly Leu Pro Leu Ala Asp Ala Ile Asp Thr Leu Val
            195                 200                 205

Leu Arg Pro Leu Gly Ala Arg Asp Thr Gly Phe Val Ala Arg Asp Ala
        210                 215                 220

Ala Arg Leu Ala Thr Pro Tyr Val Asn Asp Thr Pro Gln Pro His Arg
225                 230                 235                 240

Leu Ala Glu Asn Glu Thr Val Pro Ile Phe Asp Gly Thr Val Gly Val
                245                 250                 255

Thr Tyr Ser Pro Ser Arg Ala Leu Asp Ala Asp Ala Phe Pro Ser Gly
            260                 265                 270

Gly Ala Gly Met Val Gly Thr Ala Gly Asp Val Leu Asn Leu Leu Asp
            275                 280                 285

Thr Leu Arg Ala Gly Gly Ser Leu Leu Pro Ala Asp Leu Val Asp
        290                 295                 300

Glu Met Gly Arg Ala His Thr Gly Asn Leu Glu Leu Pro Asp Leu Pro
305                 310                 315                 320

Gly Ala Gly Phe Gly Ile Gly Phe Ser Val Leu Arg Asp Pro Leu Ala
                325                 330                 335

Ala Ala Ser Pro Glu Ser Val Gly Thr Trp Arg Trp Gly Gly Val Tyr
```

```
                    340                 345                 350
Gly His Ser Trp Phe Val Asp Arg Ala Arg Gly Leu Thr Val Val Ser
            355                 360                 365

Leu Ser Asn Thr Leu Tyr Glu Gly Met Asn Gly Gln Tyr Thr Ile Asp
    370                 375                 380

Leu Arg Asp Ala Ile Tyr Gly Ala Gly
385                 390
```